United States Patent
Mannhalter et al.

(12) 
(10) Patent No.: US 6,372,221 B2
(45) Date of Patent: *Apr. 16, 2002

(54) IMMUNOGENIC CONSTRUCTS COMPRISING FLAVIVIRUSES OR FLAVIVIRUS DERIVATIVES

(75) Inventors: Josef W. Mannhalter; Heinz Leibl; Martha Leibl, all of Vienna (AT)

(73) Assignee: Bio-Products & Bio-Engineering Aktiengesellschaft, Vienna (AT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,397

(22) PCT Filed: May 15, 1996

(86) PCT No.: PCT/EP96/02098
§ 371 Date: Dec. 12, 1997
§ 102(e) Date: Dec. 12, 1997

(87) PCT Pub. No.: WO97/00322
PCT Pub. Date: Jan. 3, 1997

(30) Foreign Application Priority Data
Jun. 14, 1995 (DE) .......................... 195 21 705

(51) Int. Cl.[7] ..................... A61K 39/295; A61K 39/385
(52) U.S. Cl. ........................ 424/196.11; 424/197.11; 424/201.1; 424/218.1; 424/239.1; 424/281.1; 424/93.3; 424/93.6
(58) Field of Search ............ 424/196.11, 197.11, 424/201.1, 218.1, 239.1, 281.1, 282.1, 93.2, 93.6; 435/69.3; 536/23.72

(56) References Cited

U.S. PATENT DOCUMENTS

| | | | | |
|---|---|---|---|---|
| 5,006,334 A | * | 4/1991 | Stevens | 424/88 |
| 5,182,109 A | * | 1/1993 | Tamura et al. | 424/92 |
| 5,494,671 A | * | 2/1996 | Lai et al. | 424/218.1 |

FOREIGN PATENT DOCUMENTS

| | | |
|---|---|---|
| WO | WO 92/03545 | 3/1992 |
| WO | WO 93/06214 | 4/1993 |

OTHER PUBLICATIONS

Leibl et al., Adjuvant/carrier activity of inactivated tick-borne encephalitis virus. Vaccine 16(4):340–345, 1998.*
*Vaccine Design The Subunit and Adjuvant Approach*, Powell et al., Eds. (Plenum Press, New York, 1995), pp. 152–153.*
Stephenson, J.R., Flavivirus vaccines, Vaccine 6:471–480, 1988.*
Fonseca et al., "Recombinant Vaccinia Viruses Co–Expressing Dengue–1 Glycoproteins prM and E Induce Neutralizing Antibodies in Mice", Vaccine, vol. 12, No. 3, (1994) pp. 279–285.
Putnak et al., "Protection of Mice Against Yellow Fever Virus Encephalitis by Immunization with a Vaccinia Virus Recombinant Encoding the Yellow Fever Virus Non–Structural Proteins, NS1, NS2a and NS2b", Journal of Patent Abstract of Japan C–1224 Jul. 13, 1994, vol. 18, No. 371, "Recombinant Live Vaccine of Virus of Virus Belonging to Family Flavivirus", 6–100465 Sato.

* cited by examiner

Primary Examiner—Donna C. Wortman
(74) Attorney, Agent, or Firm—Baker Botts L.L.P.

(57) ABSTRACT

The invention concerns an immunogenic construct comprising as components (i) an inactive flavivirus or a derivative thereof, and (ii) at least one immunogenic component which is bonded to the flavivirus or adsorbed therewith. The invention further concerns a process for preparing the immunogenic construct and its use as a vaccine.

6 Claims, 1 Drawing Sheet

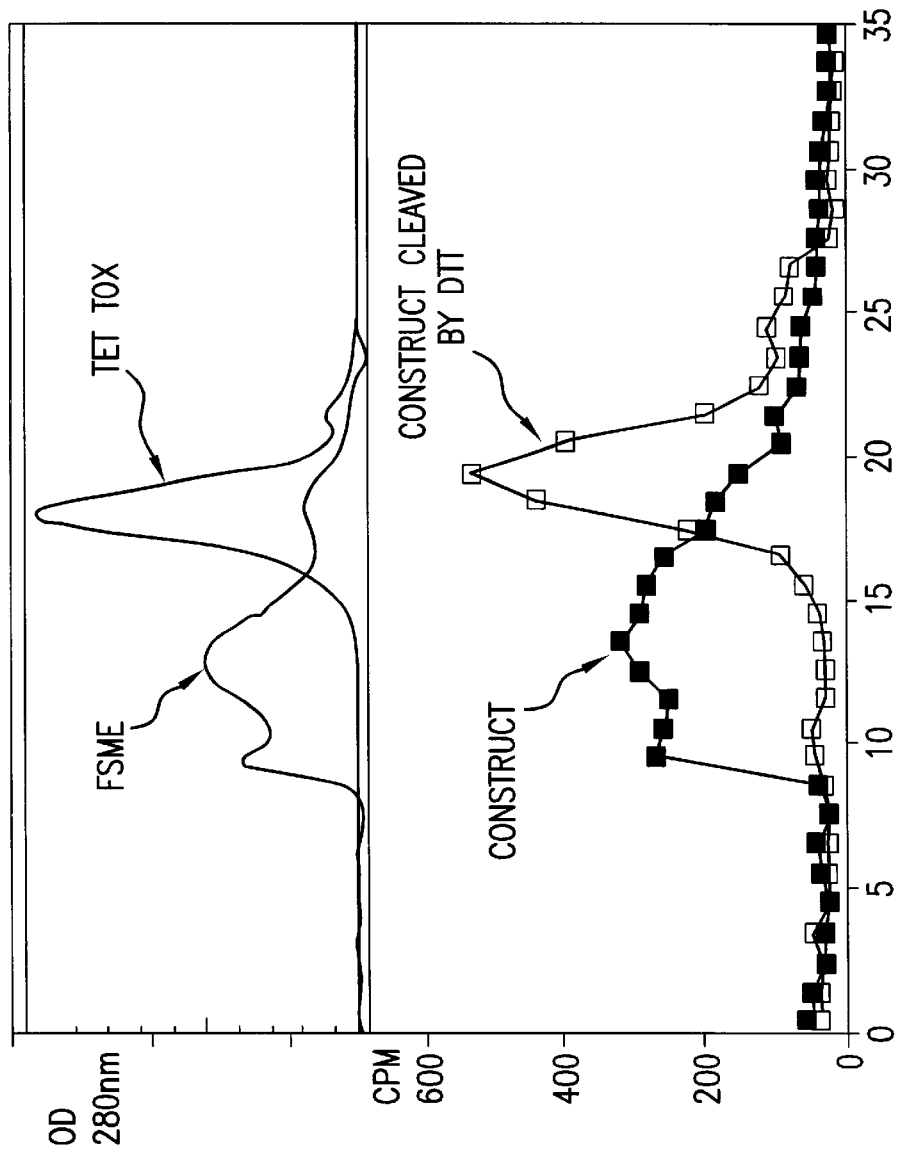

IMMUNOGENIC CONSTRUCTS COMPRISING FLAVIVIRUSES OR FLAVIVIRUS DERIVATIVES

The present invention relates to an immunogenic construct, a process for its preparation as well as its use as a vaccine.

The basis for the recognition of foreign immunogens by the immune system is still the subject of intense research. Each individual is exposed time and again to exogenous substances and it is often the case that only a weak immune response is induced against the corresponding substances.

Many vaccines are based on the use of attenuated microorganisms, for example attenuated viruses, which have the disadvantage however that they include virulent material, even if in a weakened form. These can then lead to an infection when using the corresponding attenuated microorganism to immunize humans and animals with an impaired and/or actively suppressed immune system. Disadvantages can also arise by reversion or—in the case of retroviruses—through recombination.

For these reasons, inactivated microorganisms and/or specially selected, highly purified proteins derived from the corresponding microorganism, polysaccharides or other immunogenic parts of the microorganism are more frequently being administered as vaccines instead of attenuated microorganisms. However, many of the proteins or polysaccharides and/or their epitopes known and used for this are only weakly immunogenic and the corresponding immune response, for example the formation of antibodies, is extremely weak.

Therefore, it is desirable to increase the immune response against weakly immunogenic substances and various methods for this are known in the art.

The use of adjuvants is an example of this. An adjuvant is an auxiliary agent which when administered together or parallel with an antigen increases its immunogenicity and/or influences the quality of the immune response. Hence, the adjuvant can considerably influence the extent of the humoral or cellular immune response for example. Customary adjuvants are aluminum compounds, lipid-containing compounds or inactivated mycobacteria for example. The use of particular carrier substances such as KLH (keyhole Limpet Hemocyanin) is also among the latest current methods to increase immune responses.

Aside from the bacterial products often used for increasing the immunogenicity of weakly immunogenic substances, the use of hepatitis B antigens as a carrier substance is also described in the art.

Hence, an immunogenic hybrid polypeptide consisting of hepatitis B surface antigen (HBsAg) or a fragment thereof which was bound to a further polypeptide component over a native sulfur atom is described in WO 92/11291 for example.

An immunogenic polypeptide conjugate is known from EP 0 271 302 which comprises hepatitis B core antigen (HBcAg) coupled with a further immunogenic polypeptide over an amino acid side-chain group.

A frequently described disadvantage of the hepatitis B antigens used as carrier substances is the immunodominance of these antigens when they are administered together with other immunogens. The immune response against an immunogen bound to hepatitis B antigen is only weakly pronounced by this.

Recombinant flaviviruses are known from WO 93/06214 which contain nucleic acids derived from at least two flaviviruses. These chimeric viruses contain, for example, the region of a nucleic acid which codes for a structural protein of TBEV and is combined with the region of a nucleic acid which codes for a structural protein of a flavivirus differing from TBEV, for example, Dengue virus. These chimeric viruses are described, among others, for use as live vaccines.

An object of the present invention is to provide a new immunogenic construct that enhances the immune response of a weak immunogen and simultaneously avoids the disadvantages known in the art. Additionally, a method for the production of said construct as well as the use as a vaccine are provided according to the invention.

The above problem is solved according to the invention by providing an immunogenic construct comprising as components (i) an inactive flavivirus or a derivative thereof, and (ii) at least one immunogenic component which is bound to the flavivirus and/or to the derivative.

It was surprisingly found that in binding small amounts of an immunogen to a flavivirus and/or a derivative thereof, the immune response against this immunogen is particularly enhanced. This behavior also indicates that an immune response against weak immunogens is generally enhanced through binding to a flavivirus and/or to a derivative thereof.

In the following, the inactive flavivirus is understood as a virus which no longer has the capacity to replicate in a suitable host and is therewith non-infectious.

The flavivirus is preferably an inactivated virus. For example, it can be a yellow fever virus, hepatitis C virus, Dengue virus or a Japanese Encephalitis virus. An inactive or inactivated TBE virus is particularly preferred, a TBE virus of the western subtype (FSME virus) is most preferred.

The flavivirus can be inactivated by a chemical or physical treatment. For example, a chemical treatment of the flavivirus can consist of a treatment with formaldehyde. A physical treatment can be conducted, for example, by heating and/or by a treatment with radiation (UV-irradiation, radioactive irradiation) and/or by ultrasound treatment. It can also be an attenuated virus which has been attenuated, for example, preferably by at least two mutations, by multiple passages in suitable cells or by targeted mutagenesis. The flavivirus can also be a recombinantly produced virus or a sub-viral and/or virus-like particle.

An inactivated whole virus or corresponding flavivirus antigens and/or derivatives of flavivirus are to be understood within the meaning of the invention under the term 'inactive flavivirus or a derivative thereof'.

For example, derivatives of a flavivirus can be viral fragments. Within the meaning of the invention, such fragments of a flavivirus are polypeptides, proteins, polysaccharides, nucleic acids or combinations thereof.

For example, the fragment can be a structural protein of a flavivirus or a part of a structural protein. The size of the fragments can strongly vary; a size of 10 kDa can be seen as a minimum size of the fragment.

For example, a derivative of a flavivirus can also be a chemically modified virus fragment, a synthetically produced polypeptide with analogy to a part of the flavivirus or a synthetically produced structure which increases the adjuvant property of the derivative.

The immunogenic component, which is enhanced in its immune response by the inactive flavivirus or a derivative thereof, is a protein, a polypeptide, a polysaccharide or a nucleic acid and/or a combination of two or more of the above mentioned components or an inactive microorganism. In particular embodiments, the protein, polypeptide, polysaccharide or nucleic acid is derived or originates from a virus, bacterium, fungus or parasite or is derived or originates from an allergen.

Should the immunogenic component be derived from a virus, then the virus is preferably selected from the family of the Hepadnaviridae, Herpesviridae, Poxviridae, Adenoviridae, Papovaviridae, Parvoviridae, Retroviridae, Togaviridae or Flaviviridae. For example, the virus can be HIV, herpes simplex virus, influenza virus hepatitis A, B, C, D, G, E or X.

The immunogenic component can be a protein of a virus, for example, gp160, gp120or p24 of HIV, but can also represent a different subunit of the virus, for example, a regulatory protein such as nef or rev of HIV.

The immunogen can be a so-called subunit vaccine, a recombinant vaccine, an inactive whole virus or a virus-like particle.

Should the immunogenic component be derived from a bacterium, this bacterium is preferably selected from the group Bordetella, Haemophilus, Borrelia, Pseudomonas, Corynebacteria, Mycobacteria, Streptococci, Salmonella, Pneumococci, Staphylococci, Clostridia or Helicobacter.

Should the immunogenic component originate from a parasite, then the parasite is preferably selected from the group Amaebida, Trypanosoma or Plasmodium.

Preferably, the immunogenic component differs from the inactive flavivirus or a derivative thereof. In a particularly preferred embodiment, the immunogenic component is selected from a virus group different from flaviviruses.

For formation of the claimed immunogenic construct, the inactive flavivirus or a derivative thereof and the immunogenic component are bound to each other via a covalent bond. In this connection, the claimed immunogenic construct may also be adsorbed to a carrier.

According to a further embodiment, the inactive flavivirus or a derivative thereof and the immunogenic component are bound by adsorption without formation of a covalent bond and are preferably adsorbed to a carrier.

The carrier used relates to materials as they are more closely described in the following.

The invention also comprises methods for the production of the immunogenic construct according to the invention. For example, a preferred method comprises the following steps:

(i) treating the inactive flavivirus or a derivative thereof and/or the immunogenic component with an activator suitable for covalent bonding, (ii) optionally separating excess activator, (iii) incubating the treated inactivated flavivirus and/or a derivative thereof and/or the treated immunogenic component, optionally with a non-treated flavivirus and/or derivative thereof, or a non-treated immunogenic component, under conditions which permit the formation of a covalent bond, and (iv) purifying the construct.

Homo- or preferably hetero-bifunctional cross-linkers are used as the activator for covalent bonding. Such cross-linkers are substances such as N-hydroxysuccinimide esters, imido esters, maleinimido derivatives, N-hydroxysuccinimides, pyridyl disulfides or compounds containing keto groups for example. Excess activator is optionally separated by means of dialysis, centrifugation, filtration, precipitation or with the aid of a chromatographic method.

The construct obtained with the above mentioned steps (i) to (iii) is subjected in the following to a purification. This can be conducted by means of centrifugation, filtration, precipitation, dialysis or a chromatographic method. For example, gel filtration, affinity chromatographic purification or ion exchange chromatography can be employed as chromatographic methods.

The immunogenic construct according to the invention can also be obtained in using a method which comprises the following steps:

(i) incubating the inactivated flavivirus or a derivative thereof and an immunogenic component together with an adsorbing carrier material under conditions which permit the adsorption of the components to the carrier material, and (ii) separating the construct from the non-adsorbed components.

Pharmaceutically acceptable substances are used as adsorbing carrier materials. Preferably, metals, insoluble or colloidal metal compounds or polymeric compounds and also lipid vesicles are used.

For example, noble metals such as gold or platinum or metals such as aluminum or iron are considered as metals. Insoluble or colloidal metal compounds are, among others, adjuvants such as hydroxides of aluminum, zinc or iron for example.

Polymer compounds are preferably materials as they are used for the production of resorbable and/or biodegradable materials for example. For example, biodegradable microspheres are to be named as such. Additionally, suitable polymer compounds which are not biodegradable but are physiologically accepted and tolerated (for example, latex) can also be employed according to the invention.

Lipid vesicles of various composition and size are also suitable as carrier materials.

In the above alternatives for the production of the construct according to the invention, wherein the inactivated flavivirus and/or a derivative thereof and the immunogenic component are adsorbed to the carrier, the quantitative proportions of inactivated flavivirus to immunogenic component are 200:1 to 1:200.

The construct obtained according to the above described method, which is adsorbed to a carrier material, is subsequently separated, for example, by centrifugation or filtration, and is optionally purified.

The immunogenic construct according to the invention can also be obtained by a genetic engineering method which comprises the following steps:

(i) providing at least one nucleic acid which codes for the flavivirus or a derivative thereof as well as at least one nucleic acid which codes for the immunogenic component, (ii) inserting the nucleic acids into a suitable expression system, (iii) expressing the construct encoded by the nucleic acids in suitable host cells, (iv) purifying the construct, and (v) optionally producing a bond between the components of the construct.

A nucleic acid and/or a corresponding part of the nucleic acid which codes for a flavivirus and/or a derivative thereof and/or for the desired immunogenic component is used as component (i). The latter codes for an immunogen and/or an epitope which is derived from a virus, bacterium, a fungus or parasite. The virus, bacterium, the fungus or the parasite are selected from the groups already described above.

The construct is expressed by means of a suitable expression system, for example in viral vectors, phages or plasmids which are additionally equipped with regulatory sequences. Expression can occur in eukaryotic as well as prokaryotic cells. Preferably, expression occurs in mammalian cells.

The expressed construct can be purified according to customary methods for protein purification, for example, by means of chromatographic methods.

According to a further embodiment, the immunogenic construct according to the invention can also comprise the following components:
(i) a nucleic acid sequence for an inactivated flavivirus or a derivative thereof with adjuvant function in connection with
(ii) a nucleic acid for an immunogenic component, and
(iii) regulation sequences which ensure the expression of the nucleic acid sequences in a host.

Preferably, the above mentioned immunogenic construct is present as a viral or bacterial expression vector, as a recombinant phage or a naked DNA and/or RNA. Vaccinia virus is particularly preferred as an expression vector. When the construct is present as naked DNA and/or RNA, the corresponding DNA and/or RNA is present in a plasmid which preferably contains a promoter and/or regulatory sequences and can be directly used as such for vaccination.

The invention further encompasses a vaccine which comprises an immunogenic construct according to the invention corresponding to the various alternatives together with a suitable excipient. This vaccine is suitable to induce an immune responds against flavivirus or a derivative thereof and to simultaneously strengthen the immune response against the immunogenic component(s).

Polyvalent vaccines which contain the constructs according to the invention, wherein these constructs have different immunogenic components, are particularly advantageous. The components of the construct according to the invention, namely the inactivated flavivirus or a derivative thereof and the immunogenic component, are present in a weight ratio of 200:1 to 1:200, preferably in a ratio of 80:1 to 20:1. The optimal ratios are dependent on the type of components and must be optimized for each formulation.

The present invention also relates to pharmaceutical preparations which comprise a construct according to the invention and a pharmaceutically acceptable diluent such as an isotonic sodium chloride solution for example. This pharmaceutical preparation is present in a form suitable for parenteral or mucosal administration.

For example, parenteral administration can occur intravenous, intramuscular, subcutaneous or intradermal and the preparation is present for this as a solution, suspension or as a lyophilizate which is to be reconstituted, preferably in a suitable injection syringe. Mucosal administration can occur intranasal, oral, sublingual, intrarectal or intravaginal and the preparation is present for this purpose in a solid form packaged as tablets or in capsules, as a spray or as a suppository for example.

The pharmaceutical preparation can also be enclosed, for example, within liposomes, biodegradable microspheres or virosomes and the release can then occur by different mechanisms, for example, time-released, pulse-released or slow-released.

The invention further relates to a particular immunoglobulin preparation which is obtainable by immunization of a mammal with a construct according to the invention and subsequent isolation of the immunoglobulins from blood, serum, plasma, plasma fractions or mucosal secretions. Immunization for the production of an immunoglobulin preparation according to the invention can occur parenterally or via the mucosa.

Preferably, the immunoglobulin preparation according to the invention essentially contains IgG or IgA. Under the term 'essentially', a preparation is understood which contains between 30–100%, preferably 70–100% IgG and/or IgA with respect to the total content of immunoglobulin. Particularly preferred is an immunoglobulin preparation according to the invention which contains more than 90% IgG and/or IgA.

The immunoglobulin preparation according to the invention is preferably subjected to a method for the inactivation of viruses which may be present. Customary methods for the inactivation of viruses are considered for this, for example, treatment with detergents and/or heat treatment or a treatment according to DE 44 34 538.

The present invention also includes the use of an inactive flavivirus for the production of an adjuvant or a carrier.

A kit for the production of the construct according to the invention is also provided by the present invention. This kit contains as a component the inactive, optionally modified, flavivirus or a derivative thereof and the immunogenic component as well as an activator for covalent binding or an adsorbing carrier material.

A kit for the production of the construct according to the invention can also comprise the immunogenic component and the inactive flavivirus or a derivative thereof suitable for binding to the immunogenic component.

A reagent containing the flavivirus and/or a derivative thereof suitable for binding to an immunogenic component is also provided by the present invention. With the aid of this reagent, each desired immunogenic component, preferably a weak immunogen, can be bound to the flavivirus and/or a derivative thereof.

The reagent can be present as a solution, but also as a lyophilizate. By presenting the reagent as a lyophilizate, this is to be suitably reconstituted with water or a water-containing solvent.

The present invention also comprises the use of an inactive flavivirus or a derivative thereof for the production of an adjuvant or a carrier because an immune reaction against a further immunogenic component is enhanced by the inactive flavivirus and/or a derivative thereof. Preferably, the inactive flavivirus and/or a derivative thereof was inactivated according the methods already described above. Preferably, TBE virus, most preferably TBE virus of the western subtype, is used as a flavivirus. The inactive flavivirus or a derivative thereof for use as a adjuvant has the advantage that it is not immunodominant with respect to the immunogenic component with which it is administered, i.e. an immune reaction to the immunogenic component is not suppressed, but instead is promoted.

A further advantage with respect to other adjuvants, for example with respect to Freund's complete adjuvant (a suspension of mycobacterium in oil), is that no or hardly any side effects arise from its administration.

FIG. 1 serves for closer illustration of the invention. The upper part of FIG. 1 shows the standardization of the gel filtration column (Sephacryl S-500®) with inactivated FSME virus and/or with tetanus toxoid which serve as the starting materials for the production of the construct according to the invention.

The lower part of FIG. 1 shows the gel filtration analysis of the FSME-tetanus toxoid construct ('construct') according to the invention in which the tetanus toxoid component is radioactive labeled.

The curve profile shows that, in the case of the conjugate being present, radioactive labeled tetanus toxoid is eluted together with the FSME virus which indicates a bond between the two components.

After treatment of the construct with dithiothreitol (DTT) which leads to cleavage of the components, the radioactivity was found at that place where the uncoupled tetanus toxoid starting material appeared. It can be inferred from this that tetanus toxoid was actually covalently bound via disulfide bridges to the FSME virus before the DTT treatment.

The present invention is more closely illustrated by the following examples without limiting the invention to them.

EXAMPLE 1

Covalent Binding of Tetanus Toxoid to FSME Antigen

A. Reaction of FSME Antigen with an Activator 1 ml of a solution containing inactivated FSME viruses produced according to AT 03 58 167 in phosphate buffered sodium chloride solution (PBS), pH 7.1, was incubated with 4 µl of a 20 mM solution of N-succinimidyl-3-[2-pyridyldithio]propionate=SPDP (Pierce Chem. Co., Rockford, Ill., USA) in dimethylsulfoxide for two hours at room temperature. Subsequently, unbound SPDP was separated over a PD10 column (Pharmacia, Sweden).

B. Reaction of Tetanus Toxoid with an Activator

Tetanus toxoid (Swiss Serum Inst., Bern) was purified in using gel filtration. Therefore, 20 ml of a crude tetanus toxoid solution was applied to a 5×32 cm Sephacryl S-200® column (Pharmacia, Sweden) and eluted and fractionated with PBS at a flow rate of 2 ml/min. Fractions corresponding to a molecular weight of 110–180 kD were pooled and concentrated. 300 µl of a tetanus toxoid solution purified in this manner containing 771 µg tetanus toxoid were mixed with 4 µl of a 20 mM solution of SPDP in DMSO. After an incubation time of 2 h at room temperature, unbound SPDP was separated over a PD10 column (Pharmacia, Sweden) and a buffer exchange was carried out against a buffer containing 0.1 M sodium citrate and 0.1 M sodium chloride at pH 4.5. Subsequently, reduction was carried out for 30 min at room temperature with 40 µl of a solution of 10 mg/ml dithiothreitol dissolved in 0.1 M sodium citrate and 0.1 M sodium chloride, pH 4.5. After passage over a PD10 column which was equilibrated in PBS, the protein (tetanus toxoid) modified in the described manner was mixed with the previously modified FSME virus and incubated for 16 h at 4° C. After addition of 400 µl of iodoacetamide solution (5 mg/ml), the mixture was applied in aliquots to a FPLC® gel filtration column (Superose 6® HR 10/30, Pharmacia, Sweden) and eluted at a flow rate of 0.5 ml/min. The high molecular fractions which contained the construct were collected and the total protein was determined according to the method of Bradford (Anal. Biochem. 72 (1976) 248).

In order to perform a quantitative determination of the amount of tetanus toxoid coupled to the inactivated FSME virus, a small amount (1 µCi) of $^{125}$I-labeled tetanus toxoid was added. The $^{125}$I-labeling was previously carried out with the aid of IodoBeads™ (Pierce Chem. Co., Rockford, Ill., USA) according to the instructions of the manufacturer. The portion of bound tetanus toxoid could then be calculated by measuring the radioactivity in a gammacounter.

TABLE 1

Analysis of the tetanus toxoid-FSME construct

| | |
|---|---|
| total protein: | 23.32 µg/ml |
| tetanus toxoid: | 0.62 µg/ml |
| FSME virus: | 22.70 µg/ml |

The results of the coupling given in Table 1 lead to a weight ratio of FSME virus to tetanus toxoid of 37:1.

In order to prove that the tetanus toxoid-FSME construct according to the invention was actually covalently bound and not simply bound to the virus by adsorption of the tetanus toxoid, an aliquot of the construct containing $^{125}$I-labeled tetanus toxoid was treated for 30 minutes at room temperature with a reducing agent (50 mM dithiothreitol) which is able to cleave a disulfide bridge-containing SPDP compound of the two coupling partners). Subsequently, untreated construct as well as construct treated with dithiothreitol were applied to a Sephacryl S-500® gel filtration column (Pharmacia, Sweden), eluted and the collected fractions were measured for their content of radioactivity (see FIG. 1 and the description for this).

EXAMPLE 2

The Humoral Immune Response to Tetanus Toxoid-FSME Construct

5 Balb/c mice per group were intradermally immunized twice in 4 week intervals with 20 ng tetanus toxoid (i) in the form of the pure protein, (ii) in the form of the tetanus toxoid-FSME construct as well as (iii) in the form of a mixture of tetanus toxoid with inactivated FSME virus. In the mixture of tetanus toxoid and inactivated FSME virus, those amounts of tetanus toxoid and FSME virus were selected which corresponded to the amounts of tetanus toxoid and FSME in the construct. Animals which were only treated with FSME virus and/or animals which were treated with PBS buffer served as control groups. 14 days after the second immunization, blood was drawn, serum was isolated therefrom and this was tested for IgG antibodies against tetanus toxoid and/or FSME virus with the aid of an enzyme immunoassay.

In order to test for antibodies against tetanus toxoid, NuncMaxiSorp F96 ELISA plates were filled with 100 µl of a 10 µg/ml tetanus toxoid solution in carbonate buffer (pH 9.6). After 16 h incubation at 4° C., unbound tetanus toxoid was drawn off and free binding sites on the plate were saturated with 2% BSA (bovine serum albumin) in PBS (phosphate buffered saline). After incubation (16 h/4° C.) with the samples and/or with an internal positive control serum in different dilution steps, this was incubated for 90 min at 37° C. with peroxidase-labeled goat-anti-mouse IgG (Accurate Chem., Westbury, N.Y., USA), 1:50,000 dilution) and detected with ortho-phenylenediamine (3 mg/ml). The reaction was stopped with 2 N sulfuric acid prior to measurement in a Nunc-Immunoreader at 490 nm. The highest sample dilution having an optical density of greater than 0.2 after the color reaction was employed for evaluation. The reciprocal value of this dilution resulted in the sought after titer of the sample.

For measurement of the antibodies against FSME virus, NuncMaxiSorp F96 plates were filled with 100 µl of a 5 µg/ml FSME solution in carbonate buffer, pH 9.6. After 16 h incubation at 4° C., unbound FSME was drawn off and free binding sites on the plate were saturated with 2% BSA (bovine serum albumin) in PBS. After addition of the samples and/or a positive control serum in different dilution steps, this was incubated for 2 h at 37° C. Peroxidase-labeled goat-anti-mouse IgG (Accurate Chem., Westbury, N.Y., USA), 1:150,000 dilution) was then added, this was incubated for a further 90 min at 37° C., and detected thereafter with ortho-phenylenediamine (3 mg/ml). The reaction was stopped with 2 N sulfuric acid prior to measurement in a Nunc-Immunoreader at 490 nm. The highest sample dilution having an optical density of greater than 0.2 after the color reaction was employed for evaluation.

The reciprocal value of this dilution resulted in the sought after titer of the sample.

TABLE 2

|  | IgG anti-tetanus toxoid titer | IgG anti-FSME titer |
| --- | --- | --- |
| tetanus toxoid-FSME construct | 512,000 | 40,000 |
| tetanus toxoid + FSME mixture | 800 | 40,000 |
| tetanus toxoid | 100 | n.d.* |
| FSME antigen | n.d.* | 20,000 |
| PBS | n.d.* | n.d.* | n.d.*: not detectable

Table 2 demonstrates that the humoral immune response against tetanus toxoid, measured on hand of the IgG antibody titer, was massively strengthened with the application of the covalent construct. Administration of the tetanus toxoid only alone resulted in a weak titer, just as a mixture of the two individual components FSME and tetanus toxoid. As expected, application of FSME antigen alone and/or of PBS did not lead to any measurable IgG anti-tetanus toxoid titer.

At the same time, a clear immune response against FSME virus was stimulated, independent of the form of the FSME virus employed for the immunization (alone, in a mixture with tetanus toxoid or as a tetanus toxoid-FSME construct).

In a further animal experiment, 5 Balb/c mice per group were immunized twice in 4 week intervals with 20 ng tetanus toxoid in the form of the covalently bound tetanus toxoid-FSME construct as produced according to Example 1 as well as in the form of the tetanus toxoid-FSME construct treated and cleaved by dithiothreitol. 14 days after the second immunization, antibodies against tetanus toxoid were measured as described previously. Table 3 demonstrates that the immune response-strengthening effect which was produced by the conjugation to FSME was lost again by dithiothreitol treatment.

This result serves as proof that the construct according to the invention has a high immunogenic activity.

TABLE 3

Humoral immune response against tetanus toxoid

| Immunization with | IgG anti-tetanus toxoid titer |
| --- | --- |
| tetanus toxoid-FSME construct | 409,600 |
| tetanus toxoid-FSME construct after reduction with DTT | n.d.* |
| PBS | n.d.* | n.d.*: not detectable

EXAMPLE 3

The effect of the tetanus toxoid-FSME construct produced according to the invention on the induction of a tetanus toxoid-specific T cell memory, measured as antigen-specific T cell proliferation, was examined. Balb/c mice were immunized intradermal twice in 4 week intervals with 20 ng of tetanus toxoid alone, with FSME mixed and/or as tetanus toxoid-FSME. construct. Mice which were only treated with FSME and/or PBS buffer served as control groups. Two weeks after the last application, the spleen of the animals were removed and spleen cell suspensions were produced. For this, the spleens were cut into small pieces in HBSS suppli. (Hanks buffered salt solution with 100 IU/ml penicillin, 0.1 mg/ml streptomycin, 2 mM L-glutamine and 5% fetal calf serum) and pressed through a sieve. After filtration over cotton, the red blood cells were eliminated by ammonium chloride lysis.

The lymphocytes isolated from the spleen were then washed with HBSS suppli. by centrifugation and resuspended in RPMI 1640 medium (with 100 IU/ml penicillin, 0.1 mg/ml streptomycin, 2 mM L-glutamine, 10% fetal calf serum and $5 \times 10^{-5}$ M 2-mercaptoethanol). 200 $\mu$l of this cell suspension (cell density $5 \times 10^5$ M cells/ml) were incubated for 5 days at 37° C. and 5% $CO_2$ under addition of 2 $\mu$g tetanus toxoid or 2 $\mu$g of inactivated FSME virus or in the absence of antigens. Then, 1 $\mu$Ci $^3$H-thymidine was added and this was incubated for 4 hours at 37° C. The cells were drawn off onto a filter and $^3$H-incorporation was measured in a beta scintillation counter as the degree of cell proliferation. All experiments were conducted in quadruplicate and the average values were calculated. The results are given as delta cpm which means that the incorporated radioactivity of that group which was incubated in the absence of antigens was subtracted from the radioactivity of those groups which were incubated in the presence of either tetanus toxoid or FSME virus.

Table 4 demonstrates that the proliferation of spleen cells on tetanus toxoid was strengthened when the preceding immunization was conducted with the construct according to the invention. A cellular immune response against the FSME virus was induced at the same time, independent of how the FSME was applied.

TABLE 4

| Immunization of the mice with | Stimulation of the spleen cells with | |
| --- | --- | --- |
|  | tetanus toxoid (delta cpm) | FSME antigen (delta cpm) |
| the construct acc. to the invention (TT-SPDP-FSME) | 6,510 | 9,268 |
| a mixture of TT and FSME | 1,094 | 12,307 |
| TT | 2,541 | 1,940 |
| FSME | 985 | 7,123 |
| PBS | 110 | 1,599 |

What is claimed is:

1. A method of improving the immune response of a subject toward an antigen, comprising administering, to the subject, a therapeutic composition comprising an immunogenic construct comprising (i) a first component, comprising the antigen, bound to (ii) a second component, comprising an inactivated flavivirus, wherein the antigen is not a flavivirus antigen and wherein the amounts of first and second component administered are such that the second component acts as in immune adjuvant to the first component.

2. The method of claim 1, wherein the first component is covalently conjugated to the second component.

3. The method of claim 1, wherein the first component and the second component are both adsorbed to a carrier.

4. A therapeutic composition comprising an effective amount of an immunogenic construct comprising (i) a first component, comprising the antigen, bound to (ii) a second component, comprising an inactivated flavivirus, wherein the second component is present in an amount effective in enhancing the immunogenicity of the first component, and wherein the antigen is not a flavivirus antigen.

5. The composition of claim 4, wherein the first component is covalently conjugated to the second component.

6. The composition of claim 4, wherein the first component and the second component are both adsorbed to a carrier.

* * * * *

UNITED STATES PATENT AND TRADEMARK OFFICE
CERTIFICATE OF CORRECTION

PATENT NO.    : 6,372,221 B2
DATED         : April 16, 2002
INVENTOR(S)   : Mannhalter et al.

It is certified that error appears in the above-identified patent and that said Letters Patent is hereby corrected as shown below:

Title page,
Item [75], Inventors, "Martha Liebl," should read -- Martha Eibl --.
Item [56], References Cited, OTHER PUBLICATIONS, Punak et al.:
"ABSTRACT" should read -- ABSTRACTS --;
"Recombinant Live Vaccine of Virus of Virus Belonging" should read -- Recombinant Live Vaccine of Virus Belonging --.

Column 10,
Line 49, "in" should read -- an --.

Column 3,
Line 8, "gp120or" should read -- gp120 or --

Signed and Sealed this

Twelfth Day of November, 2002

Attest:

Attesting Officer

JAMES E. ROGAN
Director of the United States Patent and Trademark Office